US009855824B2

(12) United States Patent
Stiehler et al.

(10) Patent No.: US 9,855,824 B2
(45) Date of Patent: Jan. 2, 2018

(54) FRAGRANCING DEVICE

(71) Applicant: MAHLE INTERNATIONAL GMBH, Stuttgart (DE)

(72) Inventors: Daniela Stiehler, Harborne Birmingham West Midlands (GB); Eric Pitz, Stuttgart (DE); Daniel Eberle, Stuttgart (DE); Martin Kayser, Leonberg (DE)

(73) Assignee: MAHLE INTERNATIONAL GMBH, Stuttgart (DE)

( * ) Notice: Subject to any disclaimer, the term of this patent is extended or adjusted under 35 U.S.C. 154(b) by 24 days.

(21) Appl. No.: 15/024,470

(22) PCT Filed: Jul. 31, 2014

(86) PCT No.: PCT/EP2014/066548
§ 371 (c)(1),
(2) Date: Mar. 24, 2016

(87) PCT Pub. No.: WO2015/043803
PCT Pub. Date: Apr. 2, 2015

(65) Prior Publication Data
US 2016/0236542 A1 Aug. 18, 2016

(30) Foreign Application Priority Data
Sep. 26, 2013 (DE) .................. 10 2013 219 463

(51) Int. Cl.
*B01F 3/04* (2006.01)
*A61L 9/12* (2006.01)
*B60H 3/00* (2006.01)

(52) U.S. Cl.
CPC ............ *B60H 3/0021* (2013.01); *A61L 9/122* (2013.01); *A61L 9/125* (2013.01); *B01F 3/04085* (2013.01); *B60H 3/0035* (2013.01)

(58) Field of Classification Search
CPC .......... B01F 3/04; B01F 3/04085; A61L 9/04; A61L 9/12; A61L 9/122
(Continued)

(56) References Cited

U.S. PATENT DOCUMENTS 5,154,893 A    10/1992  Nakade
5,234,162 A *   8/1993  Sullivan .................. A61L 9/122
                                                      221/66
(Continued)

FOREIGN PATENT DOCUMENTS

CN    101314321 A    12/2008
CN    102421617 A     4/2012
(Continued)

OTHER PUBLICATIONS

International Search Report, PCT/EP2014/066548, dated Oct. 14, 2014, 3 pgs.
(Continued)

*Primary Examiner* — Robert A Hopkins
(74) *Attorney, Agent, or Firm* — Paul D. Strain, Esq.; Strain & Strain PLLC

(57) ABSTRACT

The invention relates to a fragrancing device comprising a housing, a fragrance cartridge, a closure element and a blower, wherein the fragrance cartridge and/or the blower and/or the closure element is arranged inside the housing and the housing has a first opening and a second opening, wherein an air flow can flow through the housing from the first opening to the second opening, wherein the fragrance cartridge can be exposed and closed by the closure element, wherein the first opening and/or the fragrance cartridge is arranged upstream of the blower relative to the air flow direction in the housing and the second opening is arranged downstream of the blower relative to the air flow direction in the housing.

13 Claims, 1 Drawing Sheet

(58) Field of Classification Search
USPC .................. 261/30, 107, DIG. 88; 422/124
See application file for complete search history.

(56) References Cited

U.S. PATENT DOCUMENTS 7,734,159 B2 * 6/2010 Beland .................. A61L 9/035
  392/390
2011/0027124 A1 2/2011 Albee et al.

FOREIGN PATENT DOCUMENTS

| CN | 202915471 U | 5/2013 |
| EP | 1 941 915 A1 | 7/2008 |
| GB | 2 423 930 A | 9/2006 |
| JP | 2004-24161 A | 1/2004 |

OTHER PUBLICATIONS

German Search Report, Appl. No. 10 2013 219 463.3, dated Apr. 16, 2015, 8 pgs.

* cited by examiner

FRAGRANCING DEVICE

CROSS-REFERENCE TO RELATED PATENT APPLICATIONS

This application is a National Stage of International Application No. PCT/EP2014/066548, filed Jul. 31, 2014, which is based upon and claims the benefit of priority from prior German Patent Application No. 10 2013 219 463.3, filed Sep. 26, 2013, the entire contents of all of which are incorporated herein by reference in their entirety.

TECHNICAL SCOPE

The invention relates to a fragrancing device having a housing, having a fragrance cartridge, having a closure element and having a blower, wherein the fragrance cartridge and/or the blower and/or the closure element are arranged inside the housing and the housing comprises a first opening and a second opening, wherein the housing, is traversable with an air flow from the first opening toward the second opening, wherein the fragrance cartridge is operable and closable by means of the closure element.

PRIOR ART

To increase passenger comfort and to improve the interior atmosphere, fragrancing devices which allow fragrances to be output are used in air-conditioning systems and ventilation systems for motor vehicles. Simple realizations permanently fragrance the interior or an air flow which flows past the fragrancing device. This is disadvantageous because the fragrance output is not controllable and consequently the fragrance is adapted. In order to maintain perceptibility on the part of the passenger, the amount of fragrance output in this case has to be constantly increased. In addition, permanent loading, of the interior results in fragrance contamination.

More complex fragrancing systems provide the option of actively controlling the fragrance output and thus predefining the amount of fragrance output and the time of the output.

Solutions which provide a blower inside a fragrancing device, by means of which blower it is possible to generate an air flow which serves for conveying a fragrance out of the fragrance cartridge or out of a chamber surrounding the fragrance cartridge, are known in the prior art. The air flow, in this case, is able to guide the fragrance in a targeted manner to a delivery point. This can be located, for example, in an air channel of an air-conditioning system or directly in the interior of a vehicle.

Axial blowers or radial blowers are regularly used for conveying the fragrance. An air flow, which is conveyed into a region which is provided with the fragrance, is generated by the blower. As a result, the fragrance is entrained and finally delivered.

A disadvantage of the solutions in the prior art is, in particular, that, in the case of a pressurized air flow, particularly high demands are made on the connecting points and sealing points in and around the regions of the pressurized air flow, fragrance can also be delivered in an unwanted manner through gaps between housing parts or the like. Solutions with pressurized air flow which provide a complete additional enclosure for the fragrancing device are known as an alternative to this. Weight disadvantages and consequently also cost disadvantages occur as a result of the additional housing components.

REPRESENTATION OF THE INVENTION, OBJECT, SOLUTION, ADVANTAGES

Consequently, it is the object of the invention to provide a fragrancing device which comprises a simple and as space-saving a design as possible and is optimized in relation to the prior art. In addition, is the object of the invention to provide an air-conditioning system with a fragrancing device according to the invention.

The object of the present invention is achieved by a fragrancing device with the features of claim 1.

One exemplary embodiment of the invention relates to a fragrancing device having a housing, having a fragrance cartridge, having a closure element and having a blower, wherein the fragrance cartridge and/or the blower and/or the closure element are arranged inside the housing and the housing comprises a first opening and a second opening, wherein the housing is traversable with an air flow from the first opening toward the second opening, wherein the fragrance cartridge is openable and closable by means of the closure element, wherein the first opening and/or the fragrance cartridge is arranged in the housing upstream of the blower with reference to the air flow direction and the second opening is arranged in the housing, downstream of the blower with reference to the air flow direction.

The fragrance cartridge and the associated closure element are advantageously arranged in a region of the fragrancing device from which the air is sucked by the blower. This is particularly advantageous as, as a result, the pressure generated due to the blower in the interior of the housing, is lower than in the case of a realization in which the blower conveys the air toward the fragrance cartridge. As a result of the lower pressure, the sealing measures at the opening of the fragrance cartridge and of the housing in the region in front of the blower are able be correspondingly omitted. No expensive sealing means have to be provided, for example, to seal the interfaces at the housing or at the fragrance cartridge in a gas-tight manner.

Over and above this, it can be advantageous when a fragrance chamber, which comprises an air volume which is saturatable with fragrance, is provided inside the fragrance cartridge.

An air volume which is provided inside the fragrance cartridge and can be acted upon with the fragrance in the fragrance cartridge when the fragrance cartridge is closed, is advantageous in order to achieve a defined saturation with the fragrance. The delivery of the fragrance from the carrier material into the fragrance chamber takes place advantageously as a result of natural diffusion and delivery processes.

In addition, it is expedient when the pressure generated by the blower in the region of the fragrance cartridge is lower than in a region directly behind the blower.

This can be achieved, in particular, by operating the blower such that the air volume is sucked out from the region around the fragrance cartridge and is blown out of the housing. The lower pressure allows the housing to be developed and designed in a simpler manner in the region of the fragrance cartridge as no gas-tight development is necessary due to the lower pressure. The blower is consequently advantageously developed as a suction blower.

It is also advantageous when a gas chamber is provided inside the housing, wherein a fluid communication is producible between the gas chamber and the fragrance chamber of the fragrance cartridge by opening the closure element. As a result, the fluid, which is saturated with a fragrance, is able to flow out of the fragrance chamber into the gas chamber where it can be delivered by a carrier air flow.

The gas chamber serves in an advantageous manner for mixing the fragrance from the fragrance cartridge with the air flow flowing though the housing. In an advantageous manner, the gas chamber is arranged directly adjacent the fragrance cartridges such that by opening a closure element, the fluid saturated with fragrance is able to be discharged directly between the interior of the fragrance cartridge and the gas chamber. As a result, a particularly advantageous mixing is able to be achieved between the fragrance from the fragrance cartridge and the air flow flowing through the gas chamber.

It can also be expedient when the fragrance can be sucked out of the gas chamber by the blower.

The pressure generated in the region of the gas chamber is kept low as a result of the suction. This is advantageous as the design of the ho sing and of the fragrance cartridges does not necessarily have to be gas-tight as a result.

In addition, it can be particularly advantageous when a carrier material which can be permeated with a fragrance is arranged inside the fragrance cartridge.

In an advantageous manner, the carrier material can be a non-woven material which is saturated with a fragrance. As a result of diffusion or as a result of outgassing the fragrance, the fragrance is able to be output from the carrier material into the surrounding area.

A preferred exemplary embodiment is characterized in that the housing comprises a third opening through which the fragrance cartridge is insertable into the housing or removable out of the housing.

The fragrance cartridge is preferably replaceable by means of an opening in the housing in order to ensure simple maintenance. An opening, through which a fragrance cartridge can be positioned inside the housing, can be provided, for example, for this purpose. As an alternative to this, the fragrance cartridge can also be realized in such a manner that it closes the opening itself.

It is also to be preferred when the fragrance cartridge and/or the closure element can be flowed around by an air flow.

The fragrance emerging out of the fragrance cartridge can be entrained in a particularly advantageous manner by an air flow as a result of it flowing, over or flowing around said cartridge. A particularly favorable mixing of air flow and fragrance can be ensured as a result.

In a particularly favorable development of the invention, it is additionally provided that the blower is formed by a radial blower or an axial blower. Depending on the installation space available, either a radial blower or an axial blower can be used in an advantageous manner.

In addition, it is to be preferred when the fragrance cartridge and the closure element are realized integrally as a structural unit.

Integral realization is advantageous in particular in the event of maintenance or repair as integral realization ensures simple replaceability. In a particularly advantageous development, the fragrance cartridge, the closure element and an actuator which actuates the closure element are assembled in such a manner to form a structural unit that they are able to be inserted into an receiving device in one process.

In an alternative development of the invention, it can be provided that a plurality of fragrance cartridges are providable, wherein a singular number of fragrance cartridges or a plurality of fragrance cartridges are closable by one closure element or by several closure elements.

As a result of a plurality of fragrance cartridges, a larger quantity of identical fragrances can be introduced into a fragrance device or several different fragrances can be introduced in one fragrance cartridge in each case. Insofar as the identical fragrance is provided in the different fragrance cartridges, a defined number of fragrance cartridges can remain permanently closed until the fragrance from the already used fragrance cartridges is totally exhausted. In this way, the change intervals for the individual fragrance cartridges can be extended.

For the case where different fragrances are provided, different fragrances can be generated or output, as a result of which different comfort states can be generated in the vehicle.

According, to a particularly preferred further development of the invention, it can be provided that in the interior the housing realizes a plurality of flow paths which are separate from one another, wherein one or several fragrance cartridges are assigned to each flow path.

Several flow paths, which are traversable by the air conveyed through the housing, are provided in an advantageous manner in particular in the region of the gas chamber inside the housing. The flow paths can be separated from one another, for example, by means of partition walls.

In an advantageous development, the individual flow paths each have associated therewith one or several fragrance cartridges. In this way, the fragrance flowing out of the fragrance cartridges can be guided in a targeted manner. In particular, when different fragrances are stored in the fragrance cartridges, division into individual flow paths can be advantageous in order to avoid unwanted mixing of one fragrance with another different fragrance.

The object of the present invention is additionally achieved by an air-conditioning system with the features of claim 13.

One exemplary embodiment of the invention relates to an air-conditioning system having a fragrancing device according to the invention, wherein the fragrancing device is arranged inside an air-conditioning housing or on an air-conditioning housing and fragrance is flowable through the second opening of the fragrancing device into a flow channel inside the air-conditioning system or fragrance is flowable through the second opening of the fragrancing device into a flow channel which is separate from the air-conditioning system.

It is particularly advantageous when the fragrancing device is arranged directly adjacent the air-conditioning system or even in the air-conditioning system itself. In this way, fragrancing an air flow in the air-conditioning, system or fragrancing an air flow which emerges out of the air-conditioning system is able to be realized in a simple manner without expensive, time-consuming additional air flow channels having to be provided.

In a particularly preferred embodiment, the fragrancing device is arranged in or on an air-conditioning, system, wherein the fragrance is discharged out of the fragrancing device by means of a flow channel which is not associated with the air-conditioning system.

Advantageous further developments of the present invention are described in the sub-claims and in the following description of the figures.

BRIEF DESCRIPTION OF THE DRAWINGS

The invention is explained in detail below by way of exemplary embodiments with reference to the drawings, in which.

PREFERRED REALIZATION OF THE INVENTION

Figure 1:
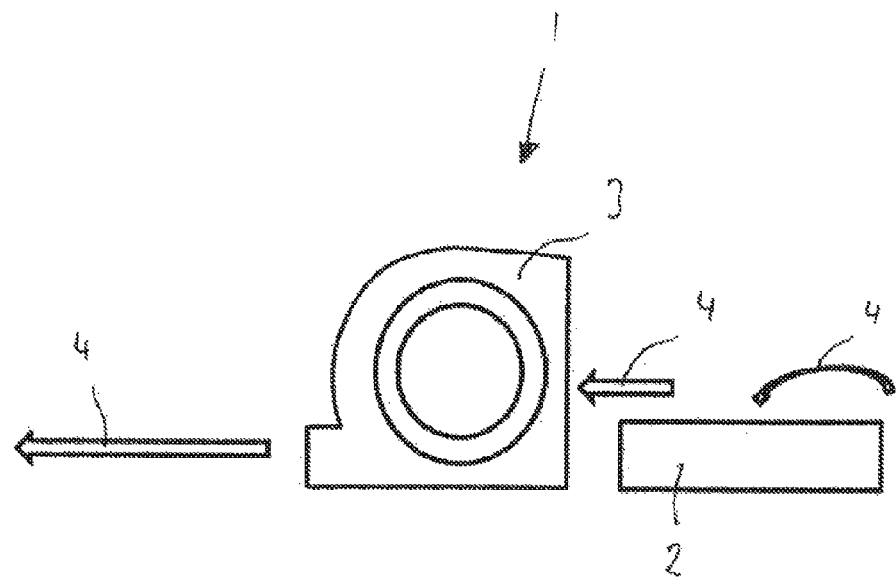
FIG. 1 shows a schematic view of the arrangement of the fragrance cartridge, the blower and an air flow which flows over the fragrance cartridge and through the blower.

FIG. 1 shows a schematic view of a fragrancing device 1. A fragrance cartridge 2 which is arranged upstream of a blower 3 is shown in FIG. 1. An air flow, which flows over the fragrance cartridge 2 and through the housing 3, can be generated the blower 3. Such an air flow is designated with the reference 4. The fragrance cartridge 2 is arranged upstream of the blower 3 in this case. The blower 3 sucks up the air above and around the fragrance cartridge 2 and blows it out along the left-hand arrow 4. The air flow above or on the fragrance cartridge 2 is consequently generated by the suction of the blower 3.

As a result of such an arrangement of the fragrance cartridge 2 or of the chamber above the fragrance cartridge in the in-take region of the blower 3, a particularly directed flow of air, which is permeated with a fragrance of the fragrance cartridge 2, can be generated at the outlet region of the blower 3. This is in particular advantageous compared to an arrangement of the fragrance cartridge 2 in the blowout region of the blower 3, as a result of which the air flow, in practice, would be pressed away above the fragrance cartridge.

Figure 2:
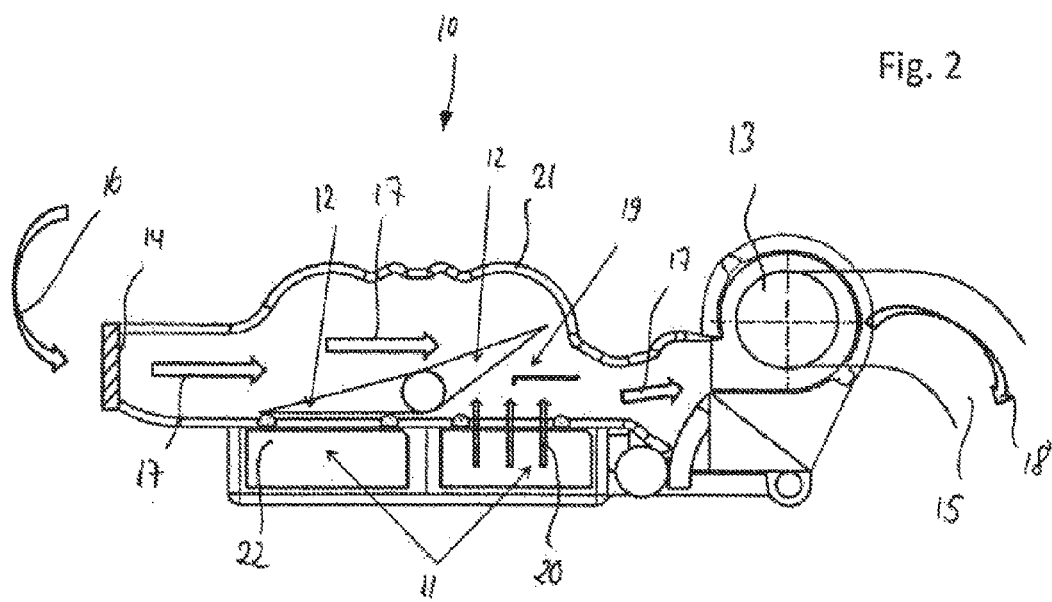
FIG. 2 shows a sectional view through a fragrancing device according to the invention.

FIG. 2 shows a sectional view through a fragrancing device 10. The fragrancing device 10 comprises a housing 21 which comprises a first opening 14 and a second opening 15. An air flow is able to flow through the first opening 14 into the housing 21 in the direction of the flow arrow designated with the reference 16. The air flow can emerge from the housing 21 by means of the second opening 15 along the flow arrow which is designated with the reference 18. The first opening 14 and the second opening 15, in this case, are preferably located on oppositely situated end regions of the housing 21.

A blower 13, which sucks in the air from the direction of the first opening 14 and blows out in the direction of the second opening 15, is arranged in the interior of the housing 21. Said operating method of the blower 13 ensures that the air volume, which is situated inside the housing 21 upstream of the blower 13, is conveyed completely out of the housing 21. The air volume inside the housing 21 which is located upstream, that is to say to the left, of the blower 13, is sucked in and blown to the right out of the second opening 15.

A gas chamber 19 is realized inside the housing 21 in the front region downstream of the first opening 14. Two fragrance cartridges 11 are arranged in said gas chamber 19. The fragrance cartridges 11 are each operable and closable by means closure elements 12. In this case, the individual closure elements 12 can be actuated in particular independently of one another such that, depending on the system default, one fragrance cartridge 11 or several fragrance cartridges 11 are opened.

Flap elements, as are shown as closure elements 12 in FIG. 2, can be used in an advantageous manner to open or to close the fragrance cartridges 11. Said elements can be mounted, for example, so as to be rotatable about an axis or can be laterally displaceable such that an opening on the fragrance cartridges 11 can be opened or closed. The closure element 12, in this case, can be driven means of an actuator such as for example, an electromotor. Gear units which translate the movement of the motor to the closure element 12 can be provided for this purpose. As an alternative to this, actuators can be provided from a shape memory alloy or a bimetal. Piezo-actuators can also be provided in alternative realizations.

In an advantageous manner, the fragrance cartridges 11 comprise in their interior a carrier material which is permeated with a fragrance. In one advantageous embodiment, said carrier material can fill out a portion of the inner volume of the fragrance cartridge 11. The fragrance can emerge or emit gas at any time and thus in the first step fill a provided air volume in the interior of the fragrance cartridge 11. Once the closure element 12 has been opened, the air volume, which is saturated with fragrance, can flow out of the fragrance cartridge into the housing 21 where it can be transported away by an air flow.

On their top surface, the fragrance cartridges 11 additionally comprise sealing elements which enable a gas-tight closure of the fragrance cartridges 11 by means of the respective closure element 12.

In the region of the fragrance cartridges 11, the housing 21 comprises an upwardly inclined region. Said region forms a gas chamber 19 in the interior of the housing 21. In said gas chamber 19, the fragrance from the fragrance cartridges 11 can be mixed with the air flow which flows through the housing 21 along the flow arrow with the reference 17. To this end, the fragrance is able to flow out of the respective fragrance cartridges 11 along the flow path 20 when the associated closure element 12 is opened.

During the operation of the blower 13, fresh air can be continuously supplied through the first opening 14 into the housing 21 along the flow arrow 16. The air flow then flows through the gas chamber 19 of the housing 21 along the flow arrow 17 and additionally into the blower 13 before the air is blown through the second opening 15 out of the housing 21 along the flow arrow 18. The discharged air, in this case, is advantageously permeated with the fragrance from the fragrance cartridges 11.

The fragrance cartridges 11 can preferably be removed out of the housing 21 individually or also as a plurality. To this end, the tub-shaped bottom segment, for example, in which the fragrance cartridges 11 are received, is able to be separated off from the housing 21 and fitted with new fragrance cartridges 11.

As an alternative to the closure elements which open or close the fragrance cartridges by means of mechanical adjusting members, an atomizer can also be provided on the fragrance cartridge which generates a release of fragrance into the gas chamber following a control signal or an electric pulse.

The fragrance cartridges 11 are preferably arranged in such a manner on one of the inside walls of the gas chamber 19 of the housing 21 that the air flow flows over the openings of the fragrance cartridges 11 along the flow arrow 17. The fragrance is discharged from the fragrance cartridges 11 and entrained in the air flow in this manner.

A carrier material which is saturated with a fragrance is arranged inside the fragrance cartridges 11. An air volume, which is also designated as the fragrance chamber 22, is realized above said carrier material. The fragrance chamber 22 is filled with fragrance emerging from the carrier material until saturation is achieved. When the corresponding closure element 12 is opened, the fragrance existing in the fragrance chamber 22 passes out of the fragrance cartridge 11 along the flow arrow 20 and is conveyed away along the direction of the flow arrow 17. The closure element 12 is also able to be opened, in this case, when the air volume in the fragrance chamber 22 is not yet totally saturated.

A fragrancing device 10, as shown in FIG. 2, can be arranged in an advantageous manner on or in a housing of an air-conditioning system or a ventilation system. In a particularly advantageous realization, the fragrancing device 10 can also be an integral component part of an air-conditioning system housing.

In an advantageous manner, the first opening 14 communicates fluidically with a region which is filled with ambient air. As an alternative to this, an already tempered air mixture can be sucked in via the opening 14 from an air-conditioning system. The flow outlet, which is effected through the second opening 15 on the right-hand end region of the fragrancing device 10, can be connected to a flow channel of an air-conditioning system which is not shown such that the fragrance bound in the air flow is able to be conveyed by the blower 13 into a predefined delivery location.

In an alternative embodiment, the second opening which is located on the right is also able to open out directly into the interior of a vehicle or into a flow channel which is separate from the air-conditioning system. The flow channel that is separate from the air-conditioning system, in this case, opens out, in turn, into the interior of a vehicle.

The individual features of FIGS. 1 and 2 can be combined together in each case. The embodiments of FIGS. 1 and 2 do not comprise any limiting character. This applies in particular with regard to the arrangement of the individual elements with respect to one another and to the sizes and the geometrical dimensions of the elements. FIGS. 1 and 2 serve to describe the inventive concept.

The invention claimed is:

1. A fragrancing device having a housing, having a fragrance cartridge, having a closure element and having a blower, wherein the fragrance cartridge and/or the blower and/or the closure element are arranged inside the housing and the housing comprises a first opening and a second opening, wherein the housing is traversable with an air flow from the first opening toward the second opening, wherein the fragrance cartridge is openable and closable by means of the closure element, wherein the first opening and/or the fragrance cartridge is arranged in the housing upstream of the blower with reference to the air flow direction and the second opening is arranged in the housing downstream of the blower with reference to the air flow direction, wherein the fragrance cartridge and the closure element are realized integrally as a structural unit.

2. The fragrancing device as claimed in claim 1, wherein a fragrance chamber, which comprises an air volume which is saturatable with fragrance, is provided inside the fragrance cartridge.

3. The fragrancing device as claimed in claim 1, wherein the pressure generated by the blower in the region of the fragrance cartridge is lower than in a region directly behind the blower.

4. The fragrancing device as claimed in claim 1, wherein a gas chamber is provided inside the housing, wherein a fluid communication is producible between the gas chamber and the fragrance chamber of the fragrance cartridge by opening the closure element.

5. The fragrancing device as claimed in claim 1, wherein the fragrance can be sucked out of the gas chamber by the blower.

6. The fragrancing device as claimed in claim 1, wherein a carrier material which can be permeated with a fragrance is arranged inside the fragrance cartridge.

7. The fragrancing device as claimed in claim 1, wherein the housing comprises a third opening through which the fragrance cartridge is insertable into the housing or removable from the housing.

8. The fragrancing device as claimed in claim 1, wherein the fragrance cartridge and/or the closure element can be flowed around by an air flow.

9. The fragrancing device as claimed in claim 1, wherein the blower is formed by a radial blower or an axial blower.

10. The fragrancing device as claimed in claim 1, wherein a plurality of fragrance cartridges are providable, wherein a singular number of fragrance cartridges or a plurality of fragrance cartridges are closable by one closure element or by several closure elements.

11. The fragrancing device as claimed in claim 1, wherein in the interior the housing realizes a plurality of flow paths which are separate from one another, wherein one or several fragrance cartridges are assigned to each flow path.

12. An air-conditioning system having a fragrancing device as claimed in claim 1, wherein the fragrancing device is arranged inside an air-conditioning housing or on an air-conditioning housing and fragrance is flowable through the second opening of the fragrancing device into a flow channel inside the air-conditioning system or fragrance is flowable through the second opening of the fragrancing device into a flow channel which is separate from the air-conditioning system.

13. An air-conditioning system having a fragrancing device having a housing, having a fragrance cartridge, having a closure element and having a blower, wherein the fragrance cartridge and/or the blower and/or the closure element are arranged inside the housing and the housing comprises a first opening and a second opening, wherein the housing is traversable with an air flow from the first opening toward the second opening, wherein the fragrance cartridge is openable and closable by means of the closure element, wherein the first opening and/or the fragrance cartridge is arranged in the housing upstream of the blower with reference to the air flow direction and the second opening is arranged in the housing downstream of the blower with reference to the air flow direction, wherein the fragrancing device is arranged inside an air-conditioning housing or on an air-conditioning housing and fragrance is flowable through the second opening of the fragrancing device into a flow channel inside the air-conditioning system or fragrance is flowable through the second opening of the fragrancing device into a flow channel which is separate from the air-conditioning system.

* * * * *